(12) United States Patent
Ito et al.

(10) Patent No.: US 9,186,282 B2
(45) Date of Patent: Nov. 17, 2015

(54) TAMPON APPLICATOR (75) Inventors: Yukihiro Ito, Kagawa (JP); Kenta Taniguchi, Kagawa (JP); Kouichi Yamaki, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 209 days.

(21) Appl. No.: 13/976,231

(22) PCT Filed: Dec. 27, 2011

(86) PCT No.: PCT/JP2011/007305
§ 371 (c)(1),
(2), (4) Date: Aug. 10, 2013

(87) PCT Pub. No.: WO2012/090488
PCT Pub. Date: Jul. 5, 2012

(65) Prior Publication Data
US 2013/0331763 A1   Dec. 12, 2013

(30) Foreign Application Priority Data
Dec. 27, 2010   (JP) .................................. 2010-290081

(51) Int. Cl.
*A61F 13/32*   (2006.01)
*A61F 13/30*   (2006.01)
*A61F 13/26*   (2006.01)

(52) U.S. Cl.
CPC ............... *A61F 13/26* (2013.01); *A61F 13/266* (2013.01)

(58) Field of Classification Search
CPC ................................ A61F 13/26; A61F 13/266
USPC .................................................. 604/14, 15, 18
See application file for complete search history.

(56) References Cited

U.S. PATENT DOCUMENTS

| 4,048,998 A | * | 9/1977 | Nigro ............................... 604/14 |
| 4,125,113 A | * | 11/1978 | Morman et al. .............. 604/227 |
| 4,198,978 A | * | 4/1980 | Nigro ............................... 604/14 |
| 4,447,222 A | * | 5/1984 | Sartinoranont ................ 604/15 |
| 4,895,559 A | * | 1/1990 | Shippert ......................... 604/15 |

(Continued)

FOREIGN PATENT DOCUMENTS

| JP | 60-6518 U | 1/1985 |
| JP | 3217617 B2 | 8/2001 |

(Continued)

OTHER PUBLICATIONS

Office Action mailed Oct. 7, 2014, corresponding to Japanese patent application No. 2010-290081.

(Continued)

*Primary Examiner* — Susan Su
(74) *Attorney, Agent, or Firm* — Hauptman Ham, LLP (57) ABSTRACT

A tampon applicator includes an outer cylinder in which an absorber is housed, and a push-out opening through which the absorber is to be pushed out is provided at one side and a grip cylinder unit is provided at the other side, and an inner cylinder which is inserted into the grip cylinder unit and being moved into the outer cylinder to be thereby able to push out the absorber outward through the push-out opening. The tampon applicator includes a grip jaw unit configured to extend from an outer circumferential face of the grip cylinder unit of the outer cylinder outwardly in a radial direction, wherein a finger hook unit by which a finger of a user is to be hooked is formed at the grip jaw unit.

12 Claims, 11 Drawing Sheets

(56) References Cited

U.S. PATENT DOCUMENTS

| | | | | |
|---|---|---|---|---|
| 5,395,309 | A * | 3/1995 | Tanaka et al. | 604/18 |
| 5,397,332 | A * | 3/1995 | Kammerer et al. | 606/151 |
| 5,437,628 | A * | 8/1995 | Fox et al. | 604/14 |
| 5,447,499 | A * | 9/1995 | Allaire et al. | 602/42 |
| 5,507,807 | A | 4/1996 | Shippert | 623/8 |
| 5,709,652 | A * | 1/1998 | Hagerty | 604/15 |
| 5,788,663 | A * | 8/1998 | Igaue et al. | 604/15 |
| 5,817,047 | A * | 10/1998 | Osborn et al. | 604/14 |
| 6,322,531 | B1 * | 11/2001 | Cortese et al. | 604/15 |
| 6,786,883 | B2 * | 9/2004 | Shippert | 604/15 |
| 7,141,036 | B2 * | 11/2006 | Berman et al. | 604/60 |
| 7,815,594 | B2 * | 10/2010 | Dougherty et al. | 604/17 |
| 7,846,171 | B2 * | 12/2010 | Kullas et al. | 606/151 |
| 7,935,098 | B2 * | 5/2011 | Bartning et al. | 604/385.17 |
| 8,075,512 | B2 * | 12/2011 | Sargent et al. | 604/15 |
| 8,529,598 | B2 * | 9/2013 | Jenson et al. | 606/213 |
| 8,961,449 | B2 * | 2/2015 | Jorgensen et al. | 604/13 |
| 2007/0021708 | A1 | 1/2007 | Bertulis et al. | |
| 2008/0119778 | A1 | 5/2008 | Jorgensen et al. | |
| 2008/0167598 | A1 | 7/2008 | Gann et al. | |
| 2008/0167599 | A1 | 7/2008 | Osborn et al. | |
| 2008/0195030 | A1 * | 8/2008 | Gann et al. | 604/15 |

FOREIGN PATENT DOCUMENTS

| | | |
|---|---|---|
| JP | 2009-500140 A | 1/2009 |
| JP | 2010-515520 A | 5/2010 |
| JP | 2010-515521 A | 5/2010 |
| WO | 2007010506 A1 | 1/2007 |
| WO | 2008084452 A1 | 7/2008 |
| WO | 2008084453 A1 | 7/2008 |

OTHER PUBLICATIONS

International Search Report and Written Opinion corresponding to PCT/JP2011/007305, dated Feb. 14, 2012.

Office Action issued Feb. 4, 2015, corresponding to Chinese patent application No. 201180062953.5.

Office Action dated Jun. 26, 2014, corresponds to Chinese patent application No. 201180062953.5.

Office Action mailed May 19, 2015, corresponding to Japanese patent application No. 2010-290081.

Office Action dated Jun. 11, 2015, corresponding to Australian patent application No. 2011353402.

* cited by examiner

TAMPON APPLICATOR

RELATED APPLICATIONS

The present application is a National Phase of International Application Number PCT/JP2011/007305, filed Dec. 27, 2011, and claims priority from Japanese Application Number 2010-290081, filed Dec. 27, 2010.

TECHNICAL FIELD

The present invention relates to a tampon applicator.

BACKGROUND ART

Conventionally, a sanitary tampon with applicator is provided. A tampon applicator is provided with an outer cylinder and an inner cylinder. An absorber having a lead-out cord is housed inside of the outer cylinder. When using the sanitary tampon, a user grips the outer cylinder, inserts the outer cylinder into a vagina, and then, compresses the inner cylinder against the outer cylinder in a state in which the user grips the outer cylinder. When the user compresses the inner cylinder against the outer cylinder, the absorber is pushed out from the outer cylinder, and then, the absorber is disposed inside of the vagina. However, when using the sanitary tampon, if the user pushes out the absorber without inserting the outer cylinder until the outer cylinder has reached an appropriate depth, the absorber could not occasionally be disposed at an appropriate position inside the vagina.

In Patent Document 1, a tampon applicator, which has been made in view of such a problem, is described. The tampon applicator is provided with a curved shaped stopper that is extensive to the periphery of an outer cylinder. When a user uses a sanitary tampon, the user compresses the outer cylinder via the stopper, and then, inserts the outer cylinder into a vagina. Then, after the outer cylinder is inserted until the outer cylinder has reached an appropriate depth, the stopper is constituted so as to abut against a vaginal opening. Therefore, the user inserts the outer cylinder until the outer cylinder has reached the appropriate depth, to be thereby able to dispose the absorber at an appropriate position inside the vagina.

CITATION LIST

Patent Literature

[PTL 1] JP Patent No. 3217617

SUMMARY OF INVENTION

Technical Problem

However, since the stopper of the tampon applicator, described in Patent Document 1, is formed in a curved shaped elliptical shape at its circumferential face, if an attempt is made to grip the stopper with fingers when it is inserted, there is an apprehension that the fingers slip. If the fingers that are gripping the stopper slip when the outer cylinder is inserted, the outer cylinder cannot be inserted in a state in which an appropriate insertion angle is maintained, and there is an apprehension that the absorber cannot be disposed at the appropriate position inside the vagina.

Therefore, the present invention has been made in view of the problem described above, and it is an object of the present invention to provide a tampon applicator, which is capable of easily disposing an absorber at an appropriate position inside a vagina.

Means for Solving the Problem(s)

In order to solve the problem above, a tampon applicator according to one aspect of the present invention includes an outer cylinder in which an absorber is housed and a push-out opening through which the absorber is to be pushed out is provided at one side of the outer cylinder and a grip cylinder unit is provided at the other side of the outer cylinder; an inner cylinder insertable into the grip cylinder unit and being moveable into the outer cylinder to be thereby able to push out the absorber outward through the push-out opening, and a grip jaw unit configured to extend from an outer circumferential face of the grip cylinder unit of the outer cylinder outwardly in a radial direction, wherein a finger hook unit by which a finger of a user is to be hooked is formed at the grip jaw unit.

Advantageous Effects of the Invention

According to the present invention, since a user inserts an outer cylinder in a state in which the user's finger is hooked on a finger hook part of a grip jaw unit, the outer cylinder can be inserted into a vagina at an appropriate position or angle inside the vagina, and it becomes possible to easily dispose an absorber at the appropriate position inside the vagina.

BRIEF DESCRIPTION OF DRAWINGS

[FIG. 1]

[FIG. 2]

[FIG. 3] FIG. 3 (a) is a plan view of the grip jaw unit, and FIG. 3 (b) is a side view of the grip jaw unit shown in FIG. 1.

[FIG. 4]

[FIG. 5]

[FIG. 6]

[FIG. 7]

[FIG. 8]

[FIG. 9]

[FIG. 10]

[FIG. 11] FIG. 11 (a) is a plan view of the grip jaw unit, and FIG. 11 (b) is a cross section of the grip jaw unit.

[FIG. 12]

[FIG. 13]

[FIG. 14] FIG. 14 (a) is a plan view of the grip jaw unit, and FIG. 14 (b) is a cross section of the grip jaw unit.

DESCRIPTION OF EMBODIMENTS (First Embodiment)

Figure 1:
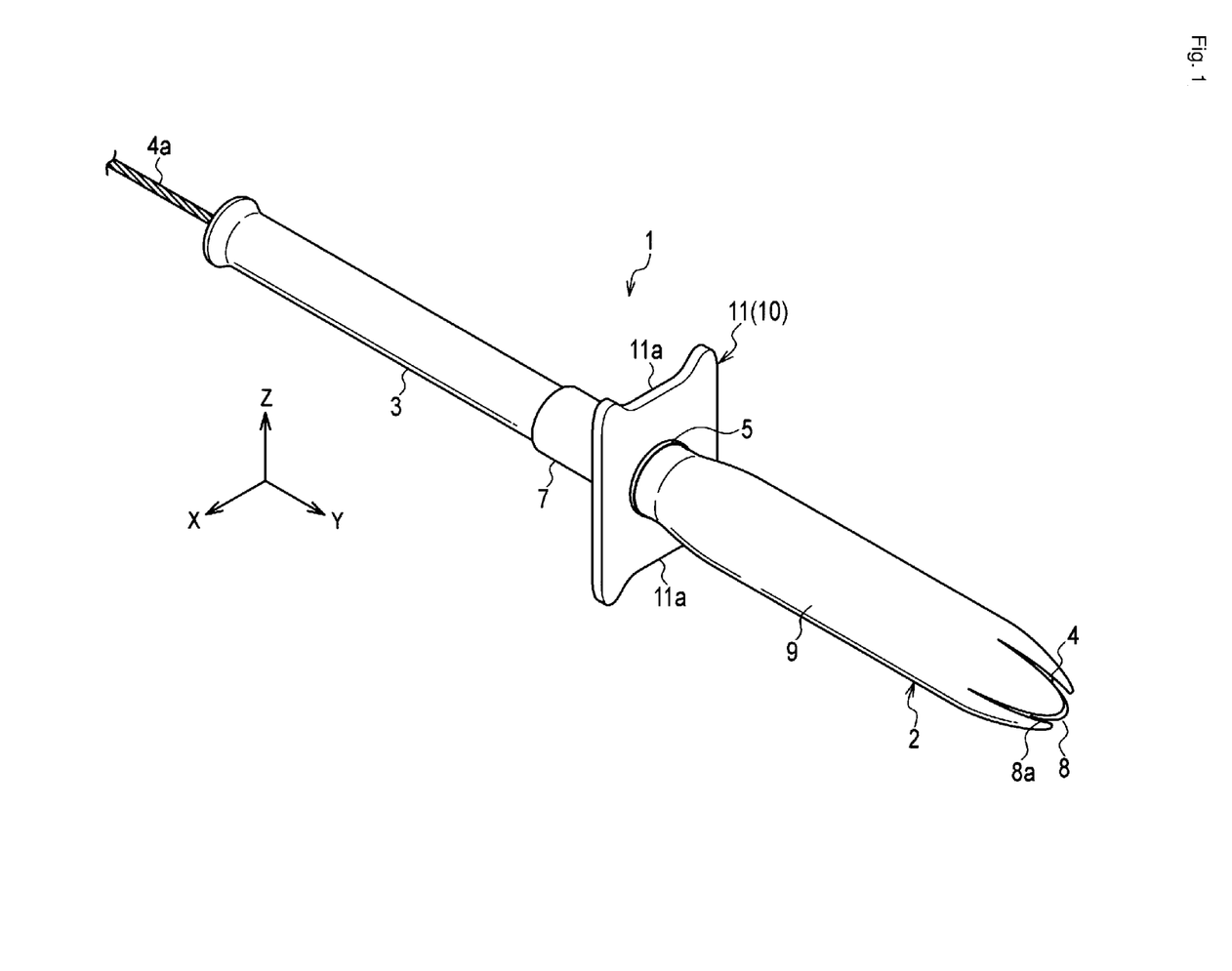
FIG. 1 is a perspective view of a tampon applicator, according to a first embodiment of the present invention.
Figure 2:
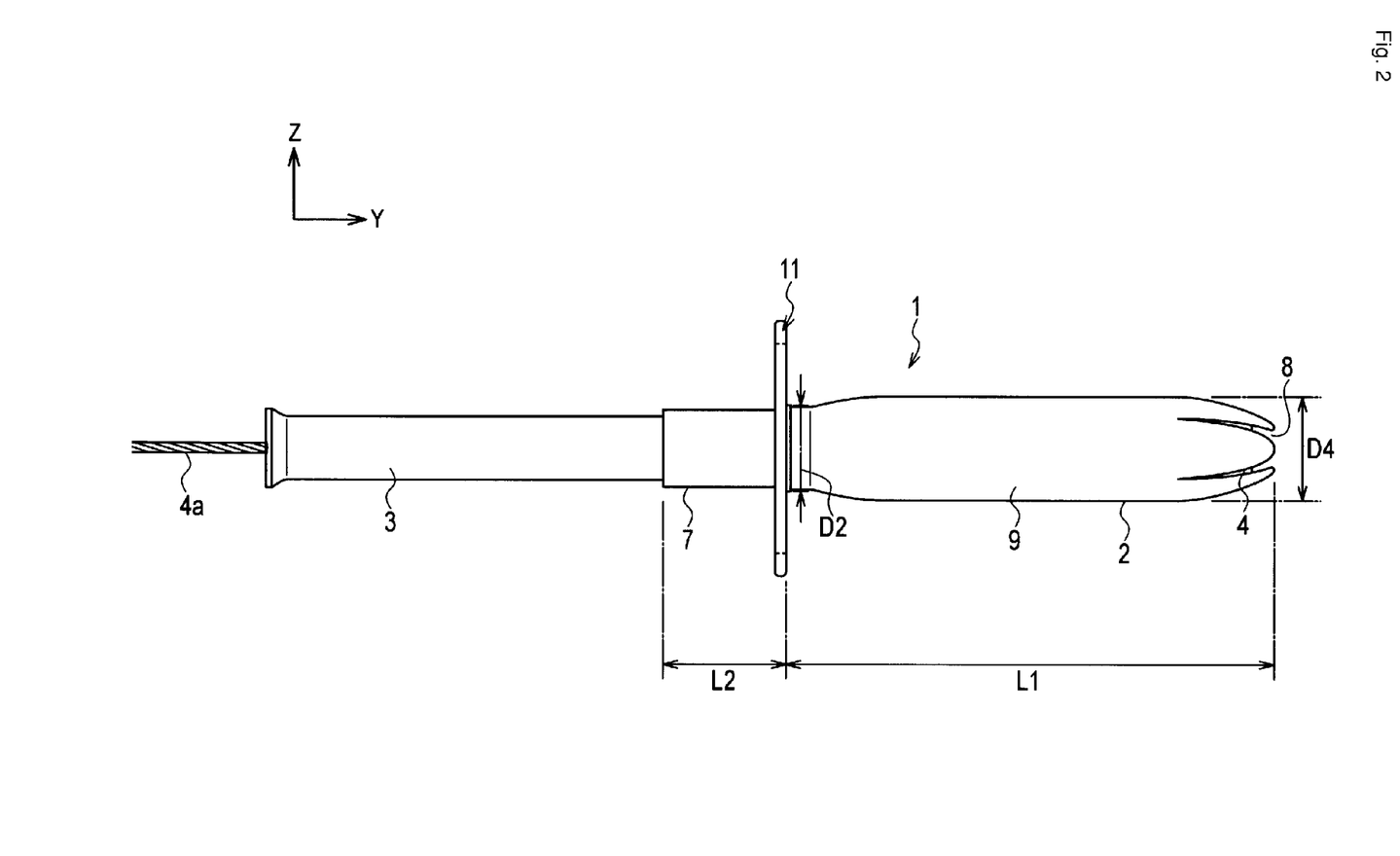
FIG. 2 is a plan view of the tampon applicator shown in FIG. 1.

A tampon applicator, according to a first embodiment of the present invention, will be described with reference to FIG. 1 and FIG. 2. FIG. 1 is a perspective view showing an entire tampon applicator, according to the first embodiment, and FIG. 2 is a plan view of the tampon applicator, shown in FIG. 1.

An applicator 1 for tampon has an outer cylinder 2 and an inner cylinder 3. The outer cylinder 2 and the inner cylinder 3 are formed in a cylindrical shape having a hollow potion at its inside. A sectional shape of each of the outer cylinder 2 and the inner cylinder 3 is a shape of a perfect circle. The outer cylinder 2 and the inner cylinder 3 are entirely formed of polyolefin such as polyethylene or polypropylene, or alternatively are entirely formed of a corrugated board, a surface of which is laminated with a polyolefin film. While the sectional shape of each of the outer cylinder 2 and the inner cylinder 3, according to the embodiment, is a shape of a perfect circle, the sectional shape of each of the outer cylinder 2 and the inner cylinder 3 may be a shape that can be easily inserted into a vagina, and for example, may be an elliptical shape.

An absorber 4 as a tampon is housed inside of the outer cylinder 2. A takeout cord 4a is coupled with the absorber 4. The takeout cord 4a inserts from an end part of the absorber 4 the inside of the inner cylinder 3, an insertion end part of which is pulled out from the inner cylinder 3. The absorber 4 can be pulled out from the inside of a body by pulling out the takeout cord 4a while in use.

A push-out opening 8 through which the absorber 4 is to be pushed out is provided at one end of the outer cylinder 2. At the push-out opening 8, a petal body 8a is formed which is deformed toward the outside in a radial direction when the absorber 4 is pushed out. While the petal body 8a is always kept to be closed at an edge part of the push-out opening 8, this petal body opens after being pushed and widened by means of the absorber 4 when the absorber 4 is pushed out by means of the inner cylinder 3. In this manner, the absorber 4 is pushed out from the outer cylinder 2 to be thereby able to insert the absorber 4 into the body.

A grip cylinder unit 7, which is to be gripped with the user's fingers at the time of moving operation of the outer cylinder 2 and the inner cylinder 3, is provided at the other end of the outer cylinder 2. The grip cylinder unit 7 has a smaller diameter than a diameter of an outer cylinder main body 9 between the push-out opening 8 and the grip cylinder unit 7. A tip end portion of the inner cylinder 3 is inserted into the grip cylinder unit 7, and a tip end face of the inserted inner cylinder 3 is seen in the absorber 4. An end part at the side of the grip cylinder unit 7 of the outer cylinder main body 9 is narrowed in a diameter that is substantially equal to that of the grip cylinder unit 7, and a convex portion 5 is formed at an outer end of the cylinder unit. The convex portion 5 abuts against a grip jaw unit 11 to be described later, restraining movement of the grip jaw unit 11 so as not to move the grip jaw unit 11 to the side of the outer cylinder main body 9.

Figure 3:
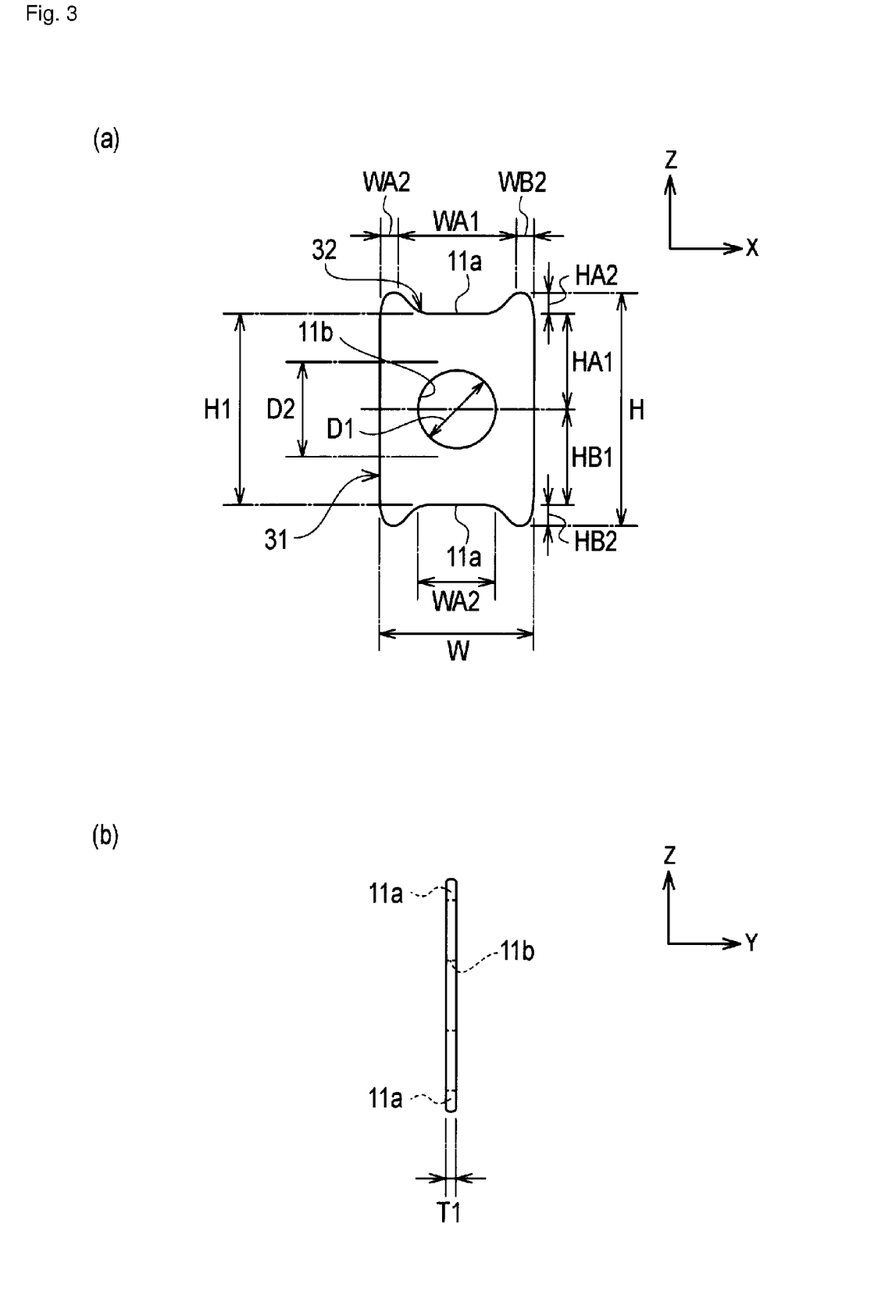

The grip jaw unit 11 configured to extend toward the outside in a radial direction more than the grip cylinder unit 7 is attached to the grip cylinder unit 7. The grip jaw unit 11 abuts against the convex portion 5. FIG. 3 is a view showing the grip jaw unit. FIG. 3 (a) is a plan view of the grip jaw unit, and FIG. 3 (b) is a side view of the grip jaw unit. A hole portion 11b through which the grip cylinder unit 7 is to be inserted is formed at the grip jaw unit 11. A diameter of the hole portion 11b may be slightly greater than a diameter of an outer circumference of the grip cylinder unit 7 or may be identical to the diameter of the outer circumference of the grip cylinder unit 7. In addition, an inner diameter D1 of the hole portion 11b of the grip jaw unit 11 is smaller than an outer diameter D2 of the convex portion 5. Therefore, the grip jaw unit 11 is movable relative to the circumferential direction and axial direction of the grip cylinder unit 7. In addition, the grip jaw unit 11 is restrained from movement to the outer cylinder main body side more than the convex portion 5, by means of the convex portion 5.

In the applicator 1 for tampon, of the embodiment, an inner diameter D1 of the grip jaw unit 11 is 9.9 mm; an outer diameter of the outer cylinder main body 9 is 13.7 mm; an outer diameter of the grip cylinder unit 7 is 9.4 mm; and an outer diameter of the convex portion 5 is 10.4 mm. In addition, a length L1 (refer to FIG. 2) from an end part of the outer cylinder 2 at the side of the push-out opening 8 to the grip jaw unit is 50 mm, and a length L2 (refer to FIG. 2) from a face at a tip end side of the grip jaw unit 11 to an end part of the outer cylinder 2 at the side of the grip cylinder unit 7 is 10 mm. Since the length L2 from the face at the tip end side of the grip jaw unit 11 to the end part of the outer cylinder 2 at the side of the grip cylinder unit 7 is equal to a length of a portion to be gripped by a user when in use, it is desirable that the length be 10 mm or more in consideration of easiness of gripping by the user.

An outer shape of the grip jaw unit 11 is a substantially rectangular shape in a planar view. The grip jaw unit 11 has: one pair of long edges 31 that extends in a longitudinal direction (a Z-direction as illustrated); and one pair of short edges 32 that extends in a widthwise direction of the grip jaw unit 11 (an X-direction as illustrated). At the short edges 32, finger hook units 11a to be hooked by the user's fingers are respectively formed. The finger hook units 11a are concave portions, each of which is concaved to the side of the hole portion 11b (a center side). The concave portions 11a are disposed so as to be opposed to each other, whereby the user can pinch the grip jaw portion 11 by her two fingers while the fingers are each placed along one of the concave portions 11a. Therefore, when the tampon applicator 1 is inserted into her body, the fingers holding the grip jaw unit 11 hardly slip. Accordingly, the outer cylinder 2 can be inserted in a state in which an appropriate insertion angle is maintained, and the absorber 4 can be easily disposed at an appropriate position inside the vagina.

A center in planar view of the grip jaw unit 11 is coincident with a center of the hole portion 11b of the grip jaw unit 11. The concave portions 11a are each formed in a predetermined region that has a dimension HA2 or HB2, in the longitudinal direction (the Z-direction as illustrated), as measured from respective end parts of the long edges 31 of the grip jaw unit 11 toward the hole portion 11b. The region in which each of the concave portions 11a is formed is further spaced, in the widthwise direction (the X-direction as illustrated), inwardly from the long edges 31 of the grip jaw unit 11 by respective spacings WA2 and WB2. A length H in the longitudinal direction of the grip jaw unit 11 is equal to a sum obtained by combining (i) distances HA1 and HB1 from the center to the regions where the concave portions 11a are formed with (ii) the dimensions HA2 and HB2 in the longitudinal direction of the regions in which the concave portions 11a are formed. In addition, a width W in the widthwise direction of the grip jaw unit 11 is equal to a sum obtained by combining (i) a dimension WA1 in the widthwise direction of the regions in which the concave portions 11a are formed with (ii) the spacings WA2 and WB2.

Dimensions of the concave portions 11a may be those determined to an extent such that a region in which the user's finger is to be hooked is ensured, and for example, may be those determined to an extent such that the user's nail can be hooked. In the embodiment, the lengths HA2 and HB2 in the longitudinal direction of the region in which the concave portions 11a are formed are respectively 3 mm, and the dimension WA1 in the widthwise direction of the region in which the concave portions 11a are formed are respectively 13 mm. It is desirable that the dimension WA1 in the widthwise direction of the regions in which the concave portions 11a are formed is such that a pad part of a finger can be received in each concave portion 11a.

In addition, in respect of the dimensions in the longitudinal direction of the grip jaw unit 11, a maximum dimension that is a length between both end parts is 26 mm, and the lengths HA 1 and HB1 from the center to the region in which the concave portions 11a are formed are respectively 10 mm. Further, in respect of the dimensions in the widthwise direction of the grip jaw unit 11, a maximum widthwise dimension that is a dimension between both end parts is 17 mm, and the dimensions WA2 and WB2 from the region in which the concave portions 11a are formed to each end in the widthwise direction are respectively 2 mm, and the linear dimension WA3 in the region in which the concave portions are formed is 10 mm.

It is desirable that a dimension in the widthwise direction of the grip jaw unit 11 be a dimension that extends outwardly by at least 2 mm more than an inner diameter of a hollow portion from a viewpoint of ensuring a strength in the circumference of the hollow portion 11b, and the dimension is 17 mm in the embodiment. Further, it is desirable that the dimension in the widthwise direction of the grip jaw unit 11 be at least 15 mm or more from a viewpoint of preventing bodily liquid from adhering to a finger when the grip jaw unit 11 and a vaginal opening 100 (refer to FIG. 4) abut against each other.

While, in the embodiment, two concave portions are provided as finger hook units, at least one concave portion may be provided without being limitative to this structure. In addition, two concave portions do not always need to be disposed to be opposed to each other, dispositions of which are not limitative thereto. In addition, while, in the embodiment, the concave portions are provided on short edges (both end parts of the long edges 31), these concave portions may be provided on the long edges 31 (both end parts of the short edges 32). However, the concave portions are provided on the short edges, whereby a distance between the concave portions becomes long in comparison with a case in which the concave portions are provided on the long edges 31, thus enabling a user to grip the grip jaw unit more easily.

A length H1 between the concave portions 11a (refer to FIG. 3) is greater than an outer diameter of the grip cylinder unit 7, and is greater than an outer diameter D4 of the outer cylinder main body 9 (refer to FIG. 2). In more detail, the length H1 of the concave portion 11a is greater than an outer diameter of the convex portion 5 that is formed at the grip cylinder unit 7. Therefore, by gripping the concave portion 11a of the grip jaw unit 11, the jaw unit can be easily held in comparison with a case of gripping an outer circumferential face or the like of the outer cylinder 2, and a force can be applied at the time of insertion. In particular, since the concave portion 11a of the grip jaw unit 11 is formed in a curved shape, and is concaved toward the inside with respect to the outer circumferential face, the user can take her fingers along a concave part of the concave portion 11a to be able to prevent her fingers from slipping at the time of inserting the outer cylinder 2.

In addition, since, the grip jaw unit 11 is rotatable with respect to the grip cylinder unit 7, when the outer cylinder 2 is inserted into the body in a state in which the grip jaw unit 11 is gripped, the grip jaw unit 11 is rotated with respect to the outer cylinder 2 to be thereby able to insert the outer cylinder 2 into the body while maintaining an appropriate angle. Specifically, an angle or an position of a hand holding the applicator 1 for tampon varies depending upon a state in which the push-out opening 8 that is a tip end of the outer cylinder 2 abuts against the vaginal opening 100 and a state in which the grip jaw unit 11 abuts against the vaginal opening 100. At this time, by rotating the grip jaw unit 11 with respect to the outer cylinder 2, a relative angle between the grip jaw unit 11 and the outer cylinder 2 can be varied to be kept in track with a variation of a position or an angle of the hand with respect to the tampon applicator. Accordingly, even in a case where an angle or a position of the hand holding the applicator 1 for tampon has varied, the user can insert the tampon applicator smoothly by appropriately applying a force to the applicator.

An outer circumferential shape of the grip jaw unit 11 is formed in a curved shape. Specifically, apart from the shape of the concave portion 11a, a crossing portion between an outer circumferential face of the grip jaw unit 11 and a plane of the grip jaw unit 11, and a crossing portion at which a long edge and a short edge 32 cross each other are also formed in a curved shape. The curved shape may be a structure which does not has an acute angled part, or alternatively, may partially include a linear shape. The outer circumferential shape of the grip jaw unit 11 is thus formed in the curved shape to be thereby able to alleviate a touch sense obtained when the user grips the grip jaw unit 11.

In addition, the grip jaw unit 11 in the embodiment is obtained by means of ejection molding of a thermoplastic resin with the use of die molding. At the time of ejection molding, the grip jaw unit 11 may be molded at the same time when the outer cylinder 2 is molded, or alternatively, may be molded separately so as to be engaged with the outer cylinder through an integral forming step in a manufacturing process. Further, the grip jaw unit 11 may be structured to be removably mounted to the outer cylinder 2, or alternatively, may be structured so that a user engage them with each other prior to use.

Figure 4:
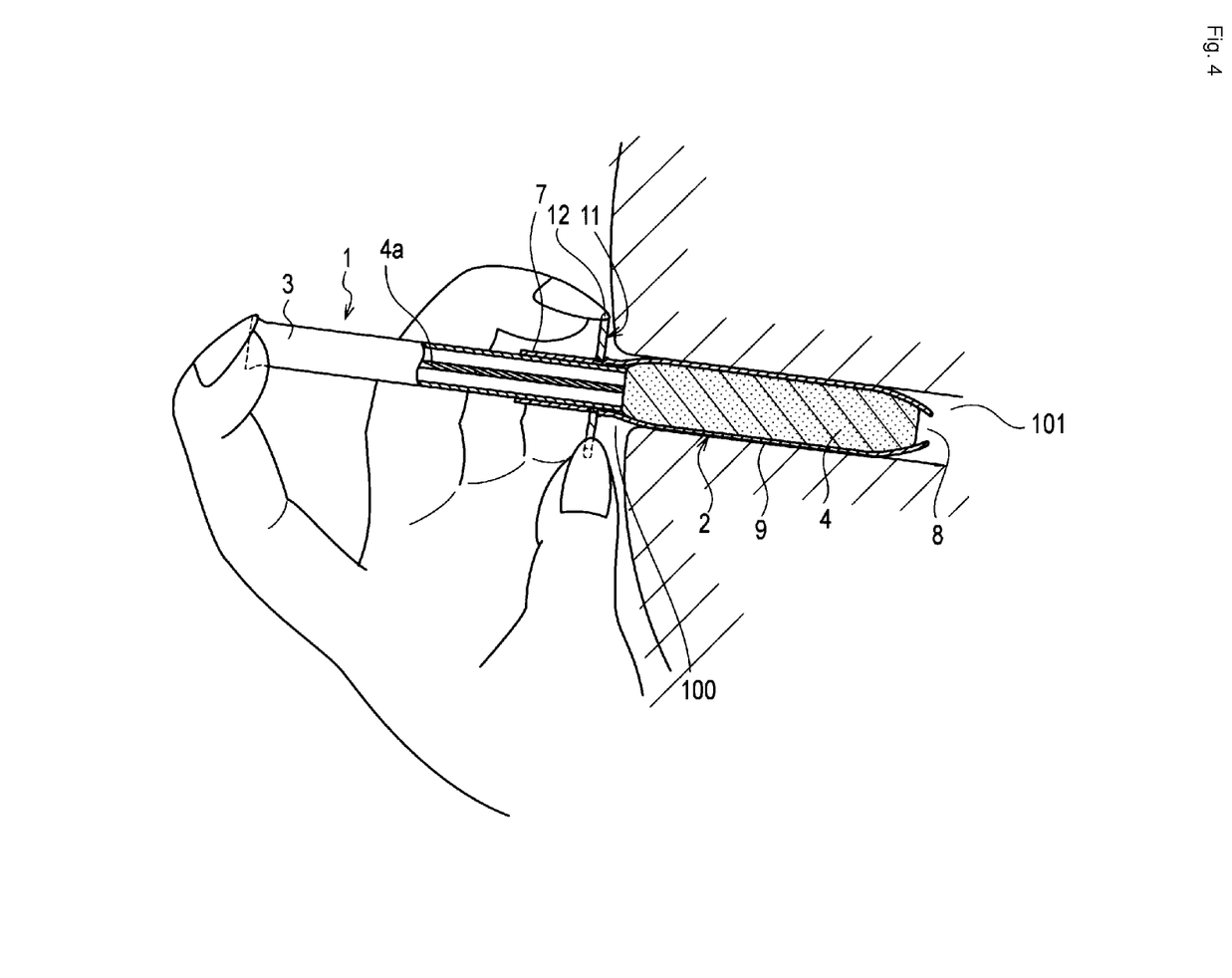
FIG. 4 is a schematic cross section showing a use mode of the tampon applicator shown in FIG. 1.

Next, use modes of the thus structured tampon applicator will be described. FIG. 4 is a schematic cross section showing a use mode of the tampon applicator. When using an absorber 4, a user first inserts an outer cylinder 2 until the cylinder has reached an appropriate position of a vagina 101. FIG. 4 shows a state in which the outer cylinder 2 is inserted until the outer cylinder has reached the appropriate position of the vagina 101. Since the user grips a grip jaw unit 11 of its diameter which is greater than that of a grip cylinder unit 7 of the outer cylinder 2, the outer cylinder can be appropriately inserted while the grip jaw unit 11 is pinched. Further, since a user pinches the grip jaw unit while per finger is taken along the concave portion, even if a user has her long finger nails or wears false nails as shown in FIG. 4, the user can orient her nails in a direction that is distant from the vaginal opening 100 to be able to prevent her nail from accidentally hitting the user's body such as the vaginal opening.

For example, if a user whose finger nails are long uses a tampon applicator, which does not have the grip jaw unit 11, since the grip cylinder unit 7 of its diameter which is smaller than that of the grip jaw unit 11 is gripped with at least two fingers, a top end of the nail may be oriented inwardly of the grip cylinder unit 7. If the outer cylinder 2 is inserted into the body in a state in which the finger nail is oriented inwardly of the grip cylinder unit 7 there is an apprehension that a tip end of the nail accidentally hits the vaginal opening 100 or its peripheral user's body. However, it is possible to prevent the nail from accidentally hitting the body by providing the grip jaw unit 11.

In a state in which the outer cylinder 2 is inserted until the outer cylinder has reached an appropriate position, a plane at a back side of the grip jaw unit 11 (at the side of the outer cylinder main body) is disposed in the vicinity of the vaginal opening. Even if an attempt is made to further insert the outer cylinder 2 in this state, the grip jaw unit 11 abuts against the user's body. That is, the grip jaw unit 11 functions as a stopper, and the user can recognize the fact that the outer cylinder 2 could be inserted until the outer cylinder had reached the appropriate position when the grip jaw unit 11, which abuts the user's body in the vicinity of the vagina opening, stops the outer cylinder 2 from being inserted further. If the grip jaw unit 11 is moveable in the axial direction of the grip cylinder unit 7, an axial movement of the grip jaw unit 11 during the insertion is stopped by the convex portion 5. In this case, the convex portion 5 defines an appropriate depth at which the absorber 4 can be placed inside the vagina. In addition, in a state in which the outer cylinder 2 is inserted until the outer cylinder has reached the appropriate position, since the grip jaw unit 11 is disposed between the vaginal opening 100 and the finger, it is possible to prevent the user's finger from being dirty due to her bodily liquid such as menstrual blood.

Next, after inserting the outer cylinder 2 until the outer cylinder has reached a predetermined position inside the vagina, the user compresses inner cylinder 2 against the side of the outer cylinder 2, whereby the absorber 4 is pushed out through the push-out opening 8 of the outer cylinder 2, and the absorber 4 is disposed at an appropriate position inside the vagina 101. In this way, by providing the grip jaw unit 11, the absorber 4 can be easily disposed at the appropriate position without the user's finger touching the vaginal opening or its vicinity. By disposing the absorber 4 at the appropriate position, the user can lessen a sense of discomfort when in use, and can comfortably feel use of the tampon.

Figure 5:
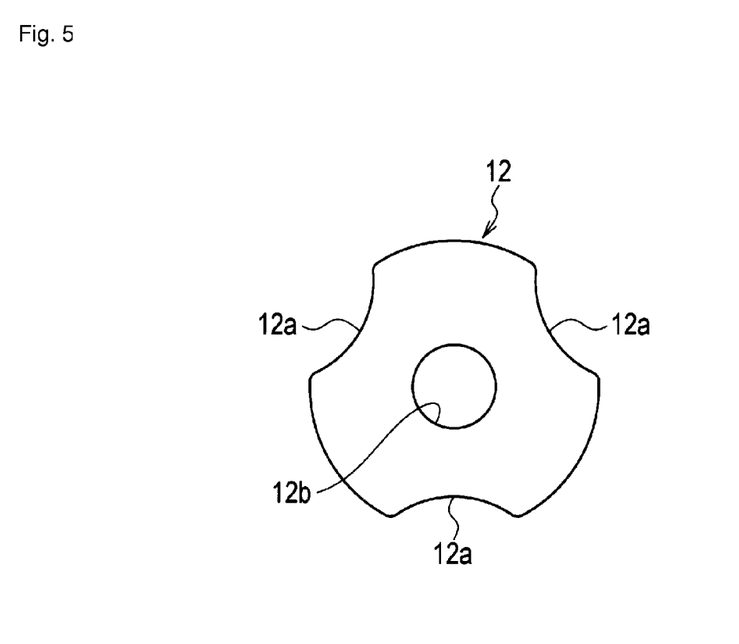
FIG. 5 is a plan view of a grip jaw unit according to Exemplary Modification 1.
Figure 6:
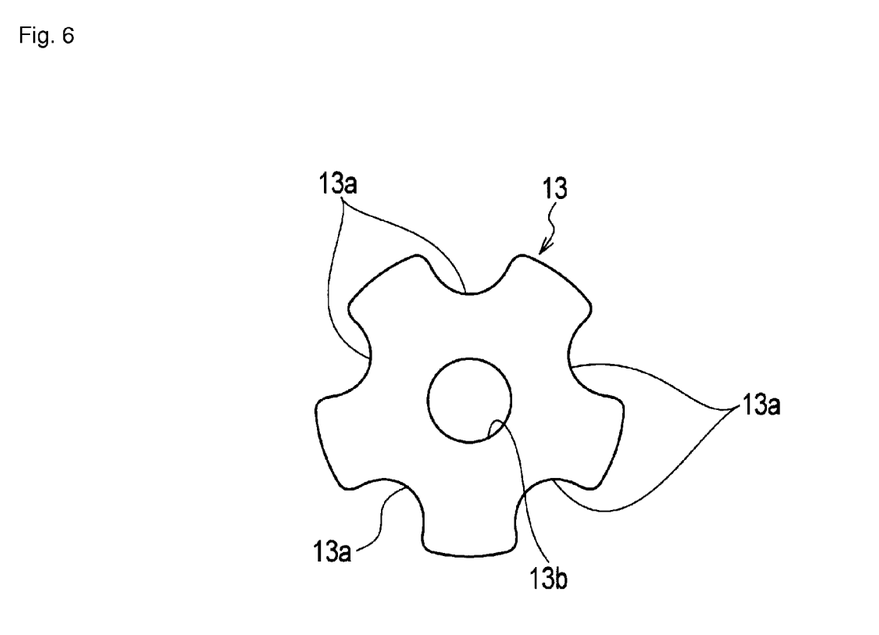
FIG. 6 is a plan view of a grip jaw unit according to Exemplary Modification 2.

The finger hook units of the grip jaw unit 11 according to the first embodiment are respectively provided on one pair of short edges, and are provided at two sites. However, the finger hook units may be provided at two sites or more of the grip jaw unit without being limitative to this structure. Next, a grip jaw unit according to Exemplary Modification will be described. FIG. 5 is a plan view of a grip jaw unit 12 according to Exemplary Modification 1, and FIG. 6 is a plan view of a grip jaw unit 13 according to Exemplary Modification 2. From the following description of the exemplary modifications, a description of like constituent elements of the first embodiment.

An external shape of the grip jaw unit 12 according to Exemplary Modification 1 is a substantial circular shape in planar view. On an outer circumferential face of the grip jaw unit 12, a concave portion 12a that is concaved to the side of a hole portion 12b (to the center side) is formed as a finger hook unit. A total of three concave portions 12a are formed, the intervals among the concave portions 12a are equal to each other, and the three concave portions 12a are disposed to be displaced from each other by 120 degrees with respect to a center of the hollow portion 12b. The three concave portions 12a are thus provided along an outer circumferential face of the grip jaw unit 12, whereby the grip jaw unit 12 can be gripped by three fingers, and stability at the time of inserting the outer cylinder 2 can be improved. Further, the intervals among the three concave portions 12a are made equal to each other, whereby the grip jaw unit 12 can be held by equally applying a force via the concave portions 12a, and the stability at the time of gripping the recessed portions can be improved.

In addition, like a grip jaw unit 13 according to Exemplary Modification 2 shown in FIG. 6, three or more finger hook units 3 may be formed. An external shape of the grip jaw unit 13 according to Exemplary Modification 2 is a shape of a substantially perfect circle in planar view. On an outer circumferential face of the grip jaw unit, a concave portion 13a that is concaved to the side of a hollow portion 13b (a center side) is formed as a finger hook unit. A total of five same concave portions 13a including the above concave portion are formed, and the intervals among the concave portions 13a are equal to each other. According to the grip jaw unit 13, from among these five concave portions 13a, a user can hold the grip jaw unit 13 while appropriately selecting at least one concave portion 13 at which her fingers are easily disposed. Hence, it becomes possible to appropriately grip the jaw portions even in a plurality of users whose hands in size or whose fingers in length are difficult from each other.

While, in the grip jaw units according to Exemplary Modification 1 and Exemplary Modification 2, concave portions are disposed so that the intervals among the concave portions are equal to each other, these concave portions are not limitative to this structure. For example, the grip jaw unit according to Exemplary Modification 1 may be structured in such a manner that, among three concave portions, two concave portions are disposed so that intervals there between are reduced, and intervals between each of these two concave portions and another concave portion are increased. Specifically, this grip jaw unit may be structured so that lines connecting the three concave portions form an isosceles triangle.

In addition, the grip jaw unit may be formed in another external shape other than a rectangle or a perfect circle in planar view. Further, while, in the first embodiment, a concave portion is set forth as a finger hook unit, a convex portion between a concave portion and a concave portion may be employed as a finger hook unit.

Figure 7:
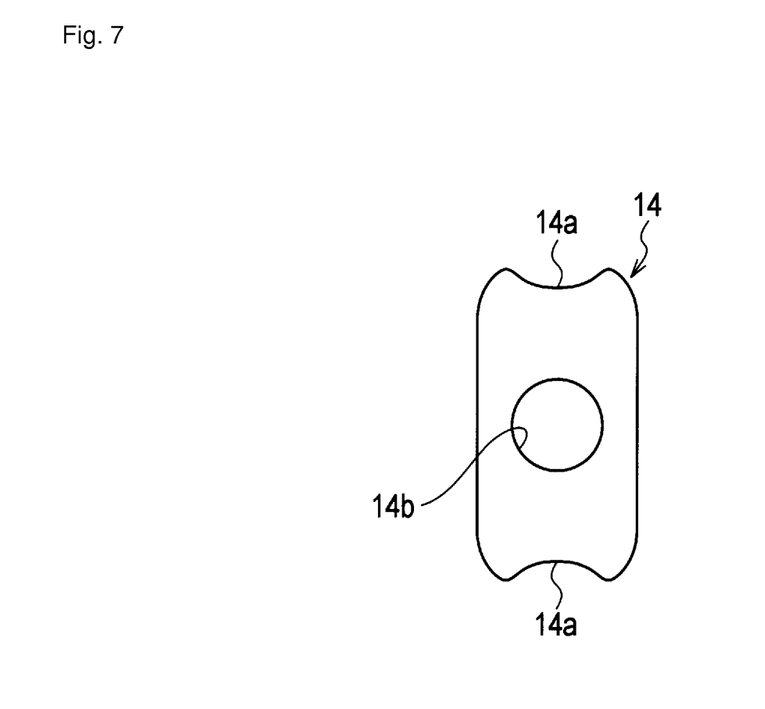
FIG. 7 is a plan view of a grip jaw unit according to Exemplary Modification 3.
Figure 8:
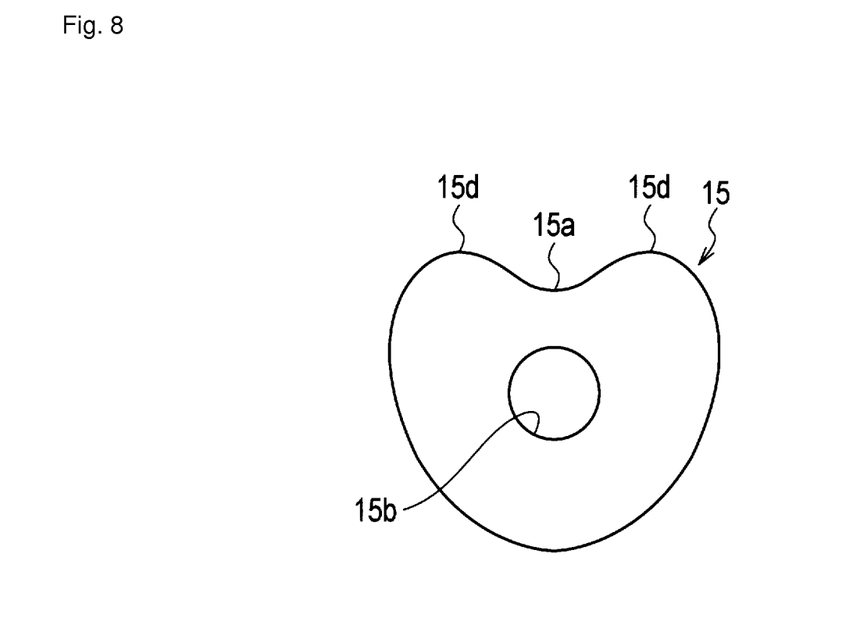
FIG. 8 is a plan view of a grip jaw unit according to Exemplary Modification 4.
Figure 9:
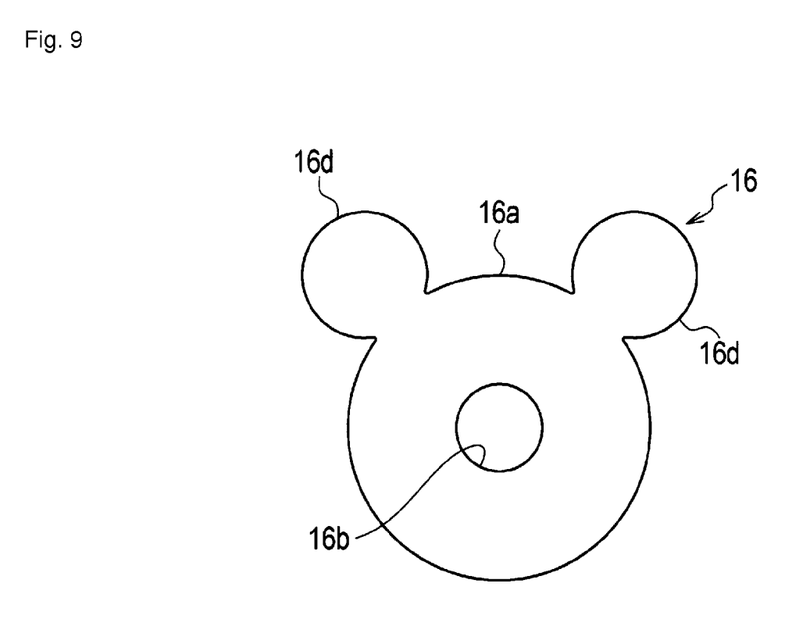
FIG. 9 is a plan view of a grip jaw unit according to Exemplary Modification 5.
Figure 10:
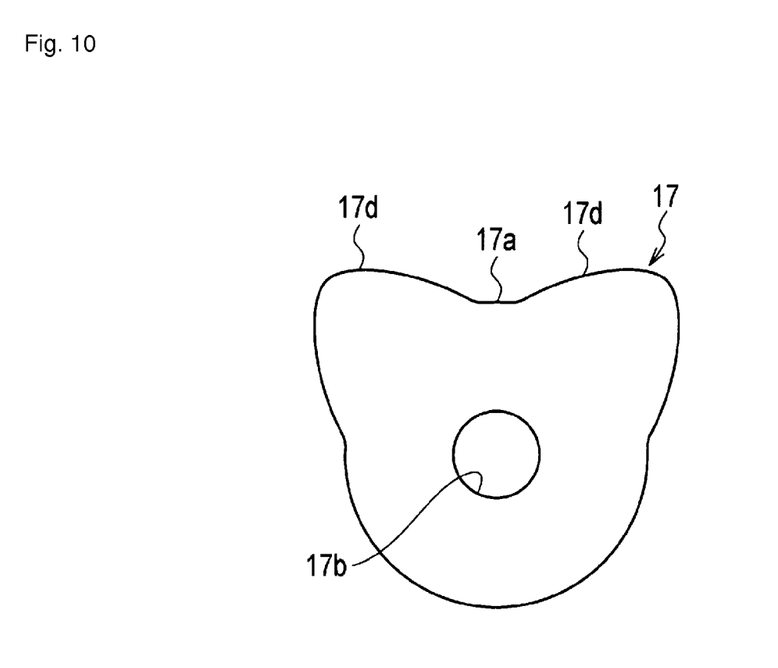
FIG. 10 is a plan view of a grip jaw unit according to Exemplary Modification 6.

Next, grip jaw units according to Exemplary Modification 3 to Exemplary Modification 6 will be described with reference to FIG. 7 to FIG. 10. FIG. 7 is a plan view of a grip jaw unit 14 according to Exemplary Modification 3, and FIG. 8 is a plan view of a grip jaw unit 15 according to Exemplary Modification 4. FIG. 9 is a plan view of a grip jaw unit 16 according to Exemplary Modification 5, and FIG. 10 is a plan view of a grip jaw unit 17 according to Exemplary Modification 6.

An external shape of the grip jaw unit 14 according to Exemplary Modification 3 is a partially elliptical shape in planar view (shorter edge side), and at both end parts in the longitudinal direction, concave portions 14a that are concaved to the side of a hole portion 14 (a center side) are respectively formed as finger hook units. These two concave portions 14a are disposed to be opposed to each other. By means of such grip jaw units 14 as well, both end parts of the grip jaw portion can be appropriately pinched with two fingers.

An external shape of the grip jaw unit 15 according to Exemplary Modification 4 is a heart shape in planar view. On an outer circumferential face of the grip jaw unit, convex portions 15d that are protruded at an upper side in the drawing and a concave portion 15a that is concaved to the center side between the convex portions 15d are formed as finger hook units. According to the grip jaw unit 15, a user can grip the grip jaw portion 15 while hooking the convex portions 15d or the concave portion 15a with fingers. In addition, since the external shape of the grip jaw unit 15 is a heart shape, a medical utensil-like tampon can be decorated lovingly by means of the grip jaw unit 15. Therefore, a gloomy feel in menstruation of a user can be alleviated, and a desire to use the tampon next time can be improved.

In addition, a user may widen the labia majora with her hand which does not hold the applicator 1 for tampon at the time of insertion of the outer cylinder 2 and, in this state, insert the outer cylinder 2 into her vagina. At this time, since the user widens the labia majora by stretching her hand from the foreside of the body, the labia majora of the foreside of the body widens, and the labia majora at the posterior side (anal side) of the body does not widen. Therefore, an opening shape of the labia majora becomes a substantially triangular shape. On the other hand, a heart-shaped grip jaw unit 15 is formed in a substantially triangular shape in planar view, and is formed in the shape that is similar to the opening shape of the labia majora. In this way, by employing the grip jaw unit, the shape of which is similar to the opening shape of the labia majora, the grip jaw unit 15 is hardly hooked on the labia majora, and the applicator 1 for tampon can be smoothly inserted into the body.

An external shape of the grip jaw unit 16 according to Exemplary Modification 5 and an external shape of the grip jaw unit 17 according to Exemplary Modification 6 are respectively shapes of animal heads in planar view. The grip jaw unit 16 is formed in a shape of a bear's head, and the grip jaw unit 17 is formed in a shape of a cat's head. A bear's ear part and a cat's ear part are more protrusive to the outside than a face part, and are convex portions 16*d* and 17*d* as finger hook units. In addition, a concave portion between the convex portions 16*d* and 17*d* that are ear parts is a respective one of concave portions 16*a* and 17*a* as finger hook units.

In this manner, the external shapes of the grip jaw units are formed in the shapes of animal heads as well, whereby a medical utensil-like tampon can be decorated lovingly by means of the grip jaw unit. Therefore, a gloomy feel in menstruation of the user can be alleviated.

In addition, a decoration effect can be further enhanced by applying a color to a grip jaw unit. Although the color to be applied to the grip jaw unit is not limitative in particular, for example, red or pink can be applied to a heart-shaped grip jaw unit, or alternatively, brown can be applied to a bear-shaped grip jaw unit. Further, by applying a color to a grip jaw unit, the grip jaw unit can be made conspicuous, and in particular, it can be easily handled in a dark location such as toilet.

(Second Embodiment)

Next, a tampon applicator, according to a second embodiment, will be described in detail with reference to FIG. 11 and FIG. 12. In the description of the second embodiment, constituent elements that are different from those of the first embodiment will be described, whereas a description of similar constituent elements is omitted therefrom.

Figure 11:
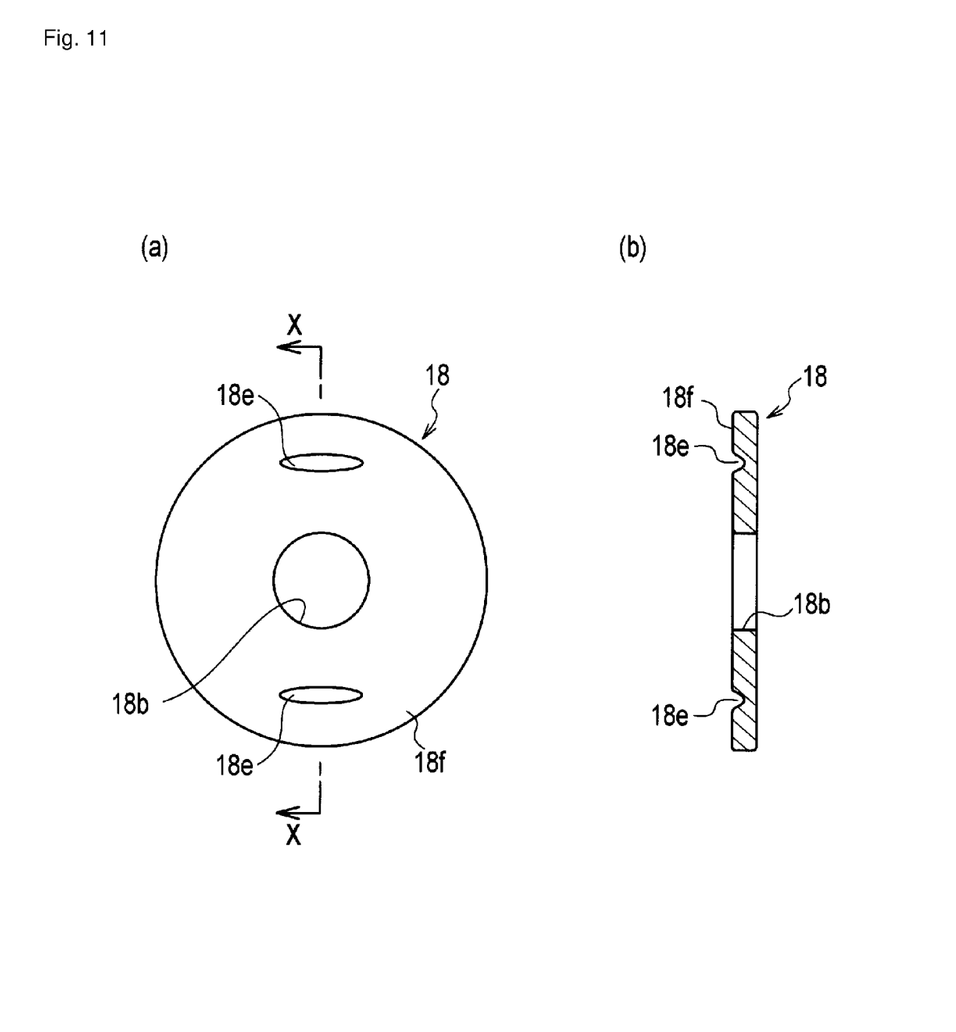
FIG. 11 is a view showing a grip jaw unit of a tampon applicator, according to a second embodiment of the present invention.

FIG. 11 is a view showing a grip jaw unit 18 of a tampon applicator, according to the second embodiment. FIG. 11 (*a*) is a plan view of the grip jaw unit, and FIG. 11 (*b*) is a cross section taken along the line x-X shown in FIG. 11 (*a*). In addition, FIG. 12 is a view showing a use mode of the tampon applicator, according to the second embodiment.

In the grip jaw unit 18 according to the second embodiment, like the grip jaw unit according to the first embodiment, a hole portion 18*b* through which a grip cylinder unit 7 of an outer cylinder 2 is to be inserted is formed, and on a surface of the hole portion, a finger hook unit is formed. The grip jaw unit 11 according to the first embodiment and the grip jaw unit 18 according to the second embodiment are different from each other in external shape and in structure of finger hook unit.

An outer circumferential shape of the grip jaw unit 18 according to the second embodiment is a shape of a perfect circle. A finger hook unit is a nail hook unit 18*e* by which a user's nail is to be hooked. The nail hook unit 18*e* is formed on a plane 18*f* that extends from the hole portion 18*b* outwardly in the radial direction, and is formed so as to be concaved in a thickness direction of the grip jaw unit 18.

Figure 12:
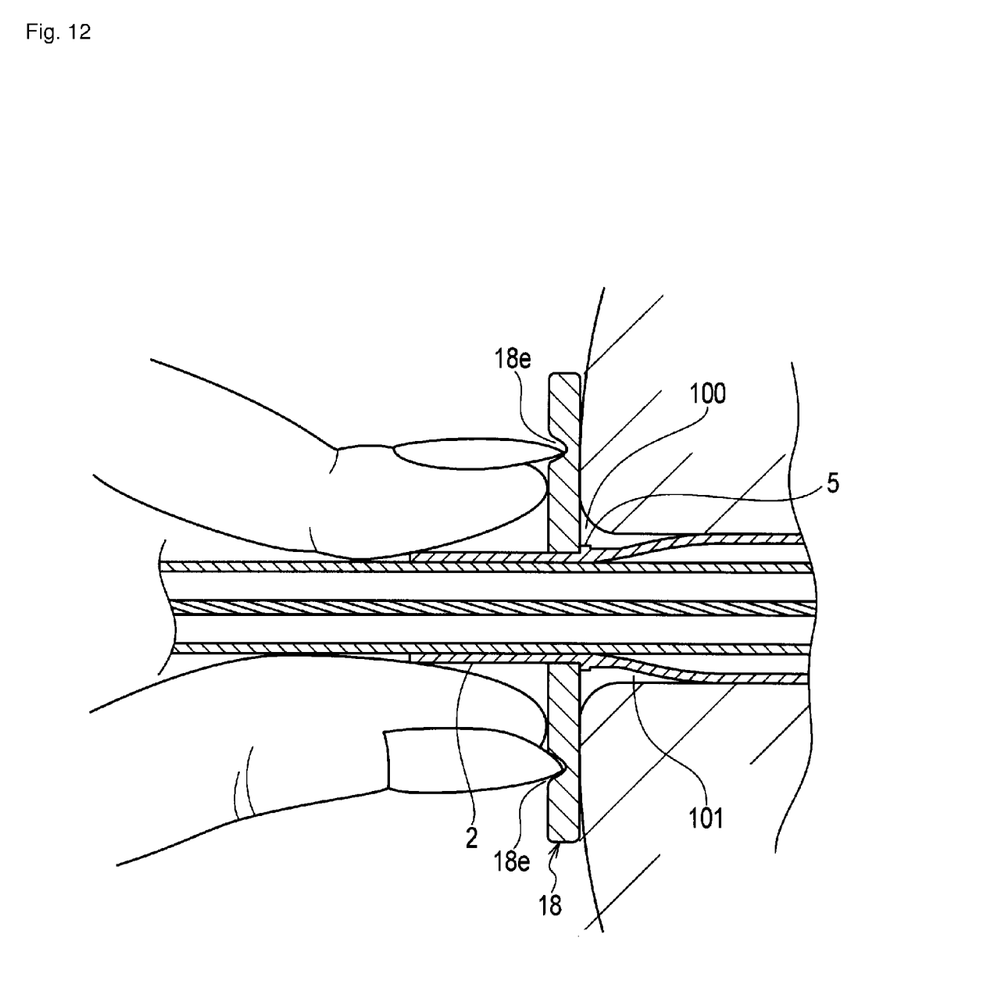
FIG. 12 is a schematic cross section showing a use mode of the tampon applicator, according to the second embodiment.

When using the tampon applicator, which is provided with the thus structured grip jaw unit 18, as shown in FIG. 12, a user inserts her finger nail into the nail hook unit 18*e* to be thereby able to insert the outer cylinder 2 into the body. In addition, for example, when the user begins to insert into the vagina with the outer cylinder 2 being abutted against the vaginal opening 100, the user grips the outer cylinder 2 at a pad part of the user's finger; and when the outer cylinder 2 is pushed at a final stage, the user inserts her nail into the nail hook unit 18*e*, whereby the outer cinder 2 may be pushed into the body via the grip jaw unit 18.

Figure 13:
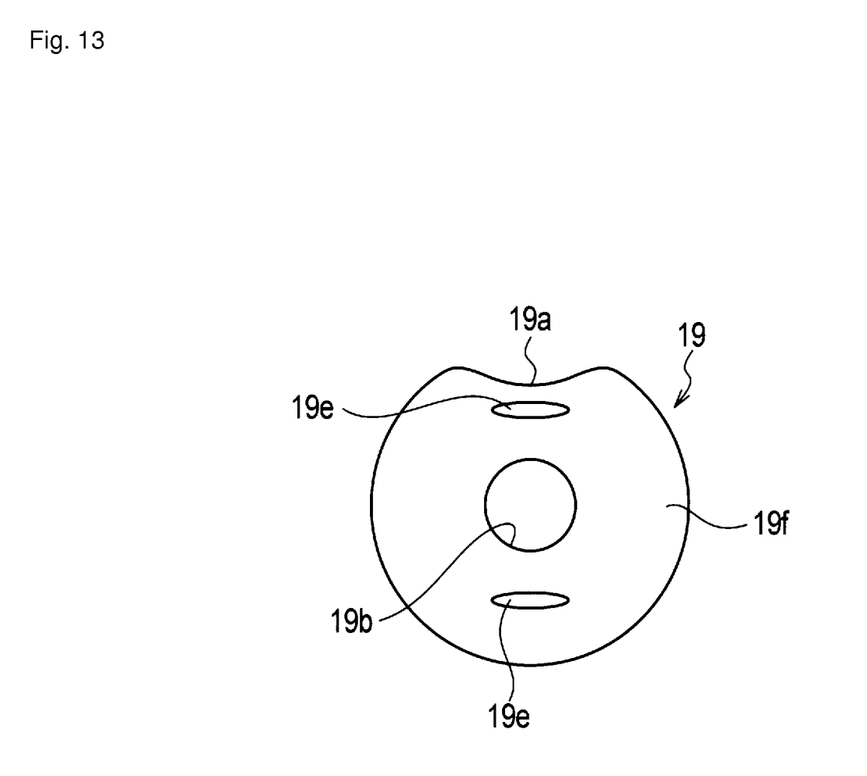
FIG. 13 is a plan view of a grip jaw unit according to Exemplary Modification 7.

In addition, the structure of the nail hook unit is not limitative to the nail hook unit 18*e* of the grip jaw unit 18 according to the second embodiment. Next, a grip jaw unit according to Exemplary Modification 7 will be described with reference to FIG. 13. FIG. 13 is a plan view of a grip jaw unit 19 according to Exemplary Modification 7.

An outer circumferential shape of the grip jaw unit 19 is a perfect circle. A finger hook unit of the grip jaw unit 19 has: a concave portion 19*a* by which a finger's pad part is to be hooked; and a nail hook unit 19*e* by which a finger's nail part is to be hooked. The concave portion 19*a* is formed in a shape that is concaved from an outer circumferential face of the grip jaw unit 19 to the side of a hole portion 19*b*.

The nail hook unit 19*e* is a hole portion that is formed on a plane 19*f* that extends from the hole portion 19*b* outwardly in a radial direction, and that penetrates the grip jaw unit 19 in the thickness direction of the grip jaw unit 19. In addition, since the grip jaw unit 19 has: a concave portion 19*a* with which a finger's pad part comes into contact; and a nail hook unit 19*e* with which a finger nail part comes into contact, the user can hold the grip jaw unit 19 while appropriately selecting any of the finger hook unit at the time of insertion.

(Third Embodiment)

Figure 14:
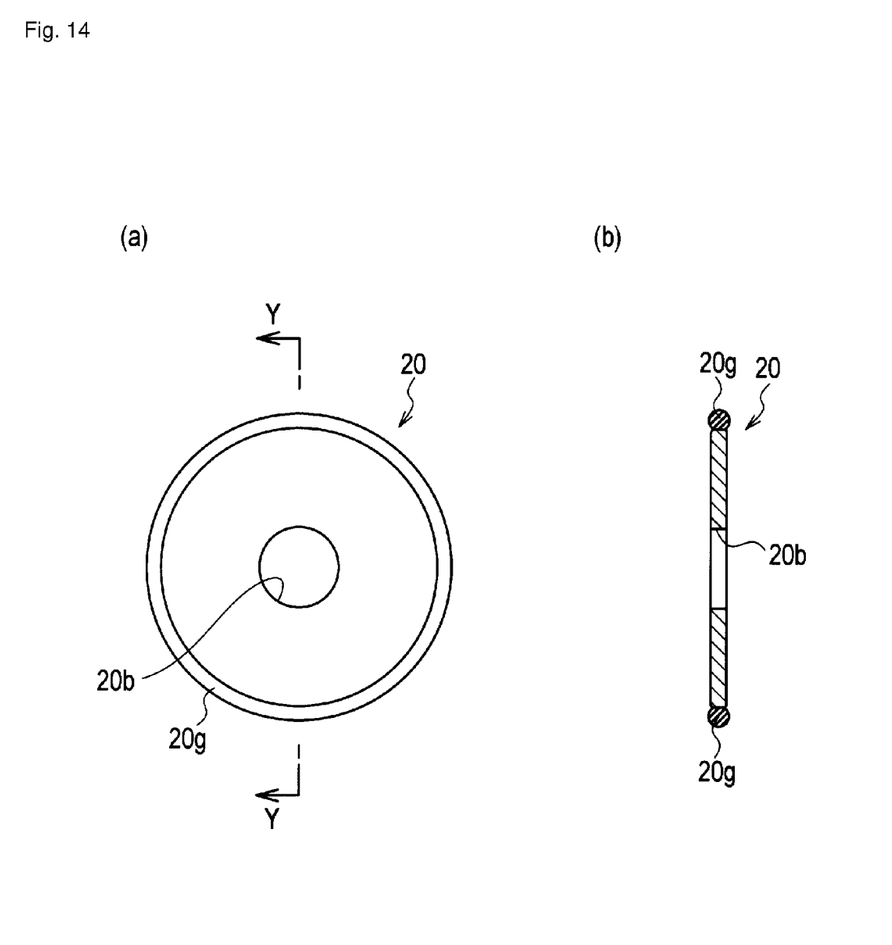
FIG. 14 is a view showing a grip jaw unit of a tampon applicator, according to a third embodiment of the present invention.

Next, a tampon applicator, according to a third embodiment, will be described in detail with reference to FIG. 14. In the description of the third embodiment, constituent elements that are different from those of the first embodiment will be described, whereas a description of similar constituent elements is omitted therefrom. FIG. 14 is a view showing a grip jaw unit of the tampon applicator, according to the third embodiment.

A grip jaw unit 20 according to the third embodiment has a rubber unit 20*g* as a finger hook unit. The rubber unit 20*g* is provided so as to cover an outer circumferential face made of an ejection-molded thermoplastic resin. According to the tampon applicator, having the grip jaw unit 20, when a user grips the grip jaw unit 20, the rubber unit 20*g* of the grip jaw unit 20 is elastically deformed, and a sense of fitting that is felt when the rubber unit is pinched with fingers can be enhanced. In addition, fingers are hardly slipped by employing the rubber unit 20*g* with its high coefficient of friction, and the tampon applicator can be inserted into the body in a state in which the grip jaw unit 20 is appropriately supported.

While, in the grip jaw unit 20 according to the third embodiment, a rubber unit is provided on an outer circumferential face, such rubber unit is not limitative to this structure.

The rubber unit may be provided on a plane that extends from the hole portion 20b of the grip jaw unit 20 outwardly in a radial direction, or alternatively, may be provided on an entire surface of the grip jaw unit.

In this manner, it is a matter of course that the present invention is inclusive of a variety of embodiments or the like that are not described herein. Therefore, a technical scope of the present invention is defined only by specific matters of the invention according to the claims that are reasonable from the foregoing description.

The present invention described above may be arranged in at least the following items:

A tampon applicator, comprising: an absorber; an outer hollow member in which the absorber is housed, the outer hollow member having opposite sides, a push-out opening through which the absorber is to be pushed out at one of the opposite sides, and a grip unit at the other side; an inner member insertable and moveable into the outer hollow member to thereby push the absorber outward through the push-out opening; and a grip jaw unit extending from an outer circumference of the grip unit of the outer hollow member outwardly in a radial direction, wherein the grip jaw unit has at least a concave portion for receiving a finger or a nail of a user for facilitating gripping of the grip jaw unit by the user's finger or nail.

Preferably, said concave portion may be arranged on a circumference of the grip jaw unit and multiple said concave portions may be arranged along the circumference of the grip jaw unit.

Preferably, said concave portion may be arranged on a plane of the grip jaw unit that faces away from the push-out opening and multiple said concave portions arranged on said plane.

Preferably, the grip jaw unit is rotatable in a circumferential direction with respect to the grip unit.

Further, the present invention described above may be arranged as a tampon applicator, comprising: an absorber; an outer hollow member in which the absorber is housed, the outer hollow member having opposite sides, a push-out opening through which the absorber is to be pushed out at one of the opposite sides, and a grip unit at the other side; an inner member insertable and moveable into the outer hollow member to thereby push the absorber outward through the push-out opening; and a grip jaw unit extending from an outer circumference of the grip unit of the outer hollow member outwardly in a radial direction, wherein the grip jaw unit has an elastically deformable element configured to be deformed by and frictionally engage a finger of a user for facilitating gripping of the grip jaw unit by the user's finger.

Preferably, the nail hook unit is concaved in a thickness direction of the grip jaw unit without extending through an entire thickness of the grip jaw unit. Further, the nail hook unit may penetrate an entire thickness of the grip jaw unit in a thickness direction of the grip jaw unit. The grip jaw unit may be moveable relative to the grip cylinder unit in an axial direction of the grip cylinder unit. The outer cylinder may further include a convex portion for limiting movement of the grip jaw unit in the axial direction and for defining an appropriate depth at which the absorber is placeale inside the user's body. The grip jaw unit may be removably mounted to the outer cylinder.

Note that this application claims the benefit of Japanese Application No. 2010-290081 the entire disclosure of which is incorporated by reference herein.

The invention claimed is:

1. A tampon applicator, comprising:
   an outer cylinder housing an absorber, the outer cylinder having:
      a push-out opening through which the absorber is configured to be pushed out, the push-out opening provided at one side of the outer cylinder, and
      a grip cylinder unit at the other side of the outer cylinder,
   an inner cylinder insertable into the grip cylinder unit and configured to move further into the outer cylinder to push out the absorber outward through the push-out opening; and
   a grip jaw unit extending from an outer circumferential face of the grip cylinder unit of the outer cylinder outwardly in a radial direction more than the grip cylinder unit,
   wherein
   the grip jaw unit has
      a first face configured to face a vaginal opening of a user,
      a second face configured to face away from the vaginal opening of the user,
      a finger hook unit configured to be hooked by a finger of the user, the finger hook unit having a concave portion arranged on an outer circumferential edge of the grip jaw unit and curving toward a center of the grip jaw unit; and
      first and second nail hook units configured to be hooked by finger nails of the user and arranged on the second face of the grip jaw unit,
   the first and second nail hook units are concave in a thickness direction of the grip jaw unit or penetrate through the grip jaw unit in the thickness direction, and
   the first nail hook unit is opposite to the second nail hook unit with respect to the center of the grip jaw unit.

2. The tampon applicator according to claim 1, wherein the finger hook unit further has a convex portion on the outer circumferential edge of the grip jaw unit.

3. The tampon applicator according to claim 1, wherein an outer circumferential shape of the grip jaw unit is a curved shape.

4. The tampon applicator according to claim 1, wherein the grip jaw unit further comprises at least two further finger hook units identical to the finger hook unit.

5. The tampon applicator according to claim 1, wherein the finger hook unit has a rubber unit that is provided on the outer circumferential edge of the grip jaw unit.

6. The tampon applicator according to claim 1, wherein the grip jaw unit is rotatable in a circumferential direction with respect to the outer cylinder.

7. The tampon applicator according to claim 1, wherein
   the grip cylinder unit has an end opposite to the push-out opening of the outer cylinder, and
   the grip jaw unit is spaced away from the end of the grip cylinder unit in a longitudinal direction of the outer cylinder.

8. The tampon applicator according to claim 1, wherein the concave portion of the finger hook unit is concave toward the center of the grip jaw unit in the radial direction.

9. The tampon applicator according to claim 1, wherein the first and second nail hook units are located within the outer circumferential edge of the grip jaw unit.

10. The tampon applicator according to claim 1, wherein the first and second nail hook units penetrate through an entire thickness of the grip jaw unit in the thickness direction.

11. The tampon applicator according to claim 10, wherein the finger hook unit is concave toward one of the first and second nail hook units in the radial direction.

12. The tampon applicator according to claim 1, wherein the first and second nail hook units are concave in the thickness direction of the grip jaw unit, without penetrating through an entire thickness of the grip jaw unit in the thickness direction.

\* \* \* \* \*